(12) United States Patent
Wang et al.

(10) Patent No.: US 8,098,021 B2
(45) Date of Patent: Jan. 17, 2012

(54) DRIVING CIRCUIT OF LIGHT EMITTING DIODE AND LIGHTING APPARATUS

(75) Inventors: Chun-Hsiung Wang, Taipei County (TW); Chih-Tsung Chen, Taipei County (TW); Hao-Yuan Wang, Taipei County (TW); Yao-Sheng Liu, Taipei County (TW); Kwan Ho, Taipei County (TW)

(73) Assignee: Cal-Comp Electronics & Communications Company Limited, New Taipei (TW)

( * ) Notice: Subject to any disclaimer, the term of this patent is extended or adjusted under 35 U.S.C. 154(b) by 425 days.

(21) Appl. No.: 12/497,544

(22) Filed: Jul. 2, 2009

(65) Prior Publication Data

US 2010/0301765 A1    Dec. 2, 2010

(30) Foreign Application Priority Data

May 26, 2009   (TW) ............................... 98209248 U

(51) Int. Cl.
*H05B 41/36* (2006.01)
*H05B 37/02* (2006.01)
(52) U.S. Cl. ........................................ 315/291; 315/307

(58) Field of Classification Search .................. 315/291, 315/294, 307, 308, 224, 312, 128
See application file for complete search history.

(56) References Cited

U.S. PATENT DOCUMENTS

| 6,057,651 | A  | * | 5/2000 | Usami ............................ 315/291 |
| 2009/0295775 | A1 | * | 12/2009 | Kim et al. ...................... 345/212 |
| 2010/0270948 | A1 | * | 10/2010 | Wang et al. ................... 315/307 |

* cited by examiner

*Primary Examiner* — Daniel D Chang
(74) *Attorney, Agent, or Firm* — Jianq Chyun IP Office

(57) ABSTRACT

A driving circuit of a light emitting diode (LED) includes a rectifier unit, a voltage-dividing circuit, a control unit, a voltage converter, a resistance and a capacitor. The rectifier unit rectifies an AC power to generate a first operation voltage. The voltage-dividing circuit generates a voltage-dividing signal. The control unit includes a regulating unit and a pulse width modulation (PWM) unit. An output terminal of the regulating unit is coupled to the PWM unit. The PWM unit outputs a PWM signal. The voltage converter adjusts a driving voltage and a driving current of the LED. The resistance is coupled between an output terminal of the regulating unit and a diode. The capacitor is coupled between a power input terminal of the regulating unit and a ground terminal. The PWM unit adjusts the PWM signal according to the voltage-dividing signal and a feedback signal output by the voltage converter.

20 Claims, 11 Drawing Sheets

DRIVING CIRCUIT OF LIGHT EMITTING DIODE AND LIGHTING APPARATUS

CROSS-REFERENCE TO RELATED APPLICATION

This application claims the priority benefit of Taiwan application serial no. 98209248, filed on May 26, 2009. The entirety of the above-mentioned patent application is hereby incorporated by reference herein and made a part of specification.

BACKGROUND OF THE INVENTION

1. Field of the Invention

The present invention relates to a driving circuit and a lighting apparatus. More particularly, the present invention relates to a driving circuit used for driving a light emitting diode, and a lighting apparatus using the same.

2. Description of Related Art

Regarding related techniques of a lighting apparatus, a dimmer is generally used for controlling a power supply, so that not only a light-emitting device (for example, a bulb) can be turned on/off, but also a light-emitting effect of the lighting apparatus can be fine-tuned. FIG. 1 is a diagram illustrating a conventional lighting apparatus. Referring to FIG. 1, the lighting apparatus 100 includes a power supply 102, a dimmer 104 and a bulb 106. The power supply 102 provides an input voltage, wherein the input voltage can be an alternating current (AC) power. When a user adjusts a light-emitting effect of the bulb 106 through the dimmer 104, the dimmer 104 can provide a voltage according to a conducting condition thereof, so as to fine-tune the light-emitting effect of the bulb 106. Further, regarding a circuit structure, the light-emitting device (for example, a conventional tungsten bulb) of the conventional lighting apparatus generally has a characteristic as that of a resistor.

With a general technology trend of energy-saving and carbon reduction, a light-emitting diode (LED) lamp gradually becomes a main option for the light-emitting devices. Therefore, based on a cost consideration, in the related art, the bulb 106 is replaced by the LED lamp while the power supply 102 and the dimmer 104 are not changed. Though, regarding the circuit structure, the LED lamp generally has a characteristic as that of a capacitor, so that when the user adjusts the brightness of the LED lamp through the dimmer 104, after the AC power output from the power supply 102 is conducted through the dimmer 104, the voltage provided by the dimmer 104 may result in a flickering phenomenon of the LED lamp.

Therefore, a dimming technique suitable for the LED lamp is provided. An output voltage adjusted by the dimmer 104 is demodulated into an internal corresponding voltage through a LED dimmable application-specific integrated circuit (ASIC), and the corresponding voltage is compared to a triangular wave to obtain a pulse. Then, the pulse drives a power transistor to control a current amount flowing through the LED, so as to achieve a dimming effect of the LED lamp. However, a complexity of peripheral circuits can be increased according to the above technique, and a fabrication cost can be increased due to a high price of a driver IC.

SUMMARY OF THE INVENTION

The present invention is directed to a driving circuit of a light emitting diode (LED), which can receive an alternating current (AC) power from a dimmer to provide a stable driving voltage and driving current to the LED.

The present invention is directed to a lighting apparatus, which can receive an AC power from a dimmer to provide a stable driving voltage and driving current, so that a LED can provide a corresponding stable brightness according to the driving voltage and the driving current.

The present invention provides a driving circuit of an LED, adapted to receive an AC power to drive the LED. The driving circuit includes a rectifier unit, a voltage-dividing circuit, a control unit, a voltage converter, a resistor and a first capacitor. The rectifier unit rectifies the AC power to generate a first operating voltage. The voltage-dividing circuit is coupled to the rectifier unit and receives the first operating voltage to generate a voltage-dividing signal corresponding to the first operating voltage. The control unit includes a regulating unit and a pulse width modulation (PWM) unit. An output terminal of the regulating unit is coupled to the PWM unit. The PWM unit outputs a PWM signal. The voltage converter is coupled between the control unit and the LED for driving the LED, and adjusting a driving voltage and a driving current of the LED according to the PWM signal. The resistor is coupled between an output terminal of the rectifier unit and a diode. Another terminal of the diode is coupled to a power input terminal of the regulating unit. The first capacitor is coupled between the power input terminal of the regulating unit and a ground terminal. The PWM unit adjusts the PWM signal according to the voltage-dividing signal and a feedback signal output by the voltage converter.

In an embodiment of the present invention, the driving circuit further includes a second capacitor coupled between an output terminal of the regulating unit and the ground terminal.

In an embodiment of the present invention, the voltage converter is coupled to the output terminal of the rectifier unit.

In an embodiment of the present invention, the rectifier unit includes a rectifier for rectifying the AC power to generate a rectified voltage.

In an embodiment of the present invention, the rectifier unit further includes a filter coupled to an output terminal of the rectifier for receiving the rectified voltage to output the first operating voltage to the voltage converter.

In an embodiment of the present invention, the rectified voltage is substantially equivalent to the first operating voltage.

In an embodiment of the present invention, the regulating unit receives the first operating voltage to output a second operating voltage to the PWM unit.

In an embodiment of the present invention, the control unit is an application-specific integrated circuit (ASIC).

In an embodiment of the present invention, the voltage converter is a buck circuit.

In an embodiment of the present invention, the AC power is an AC power adjusted by a dimmer.

The present invention provides a lighting apparatus, adapted to receive an AC power for lighting. The lighting apparatus includes an LED and a driving circuit. The driving circuit is coupled to the LED, and includes a rectifier unit, a voltage-dividing circuit, a control unit, a voltage converter, a resistor and a first capacitor. The rectifier unit rectifies the AC power to generate a first operating voltage. The voltage-dividing circuit is coupled to the rectifier unit and receives the first operating voltage to generate a voltage-dividing signal corresponding to the first operating voltage. The control unit includes a regulating unit and a PWM unit. An output terminal of the regulating unit is coupled to the PWM unit. The PWM unit outputs a PWM signal. The voltage converter is coupled between the control unit and the LED for driving the LED, and adjusting a driving voltage and a driving current of the LED according to the PWM signal. The resistor is coupled between an output terminal of the rectifier unit and a diode. Another terminal of the diode is coupled to a power input terminal of the regulating unit. The first capacitor is coupled between the power input terminal of the regulating unit and a ground terminal. The PWM unit adjusts the PWM signal according to the voltage-dividing signal and a feedback signal output by the voltage converter.

Accordingly, the lighting apparatus of the present invention includes the driving circuit of the LED and the LED, so that the lighting apparatus having the LED can be directly installed on a conventional lamp base, and a light brightness thereof can be adjusted by a conventional dimmer. The driving circuit can receive the AC power provided by the dimmer, and can continuously provide a stable driving voltage and driving current according to a duty cycle of a pulse signal and the PWM signal through bypass components of the resistors, the diode and the capacitors. Accordingly, not only the brightness of the LED of the light apparatus can be adjusted, but also a flickering phenomenon of the LED generated due to waveform variation of the AC power can be avoided.

In order to make the aforementioned and other features and advantages of the present invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
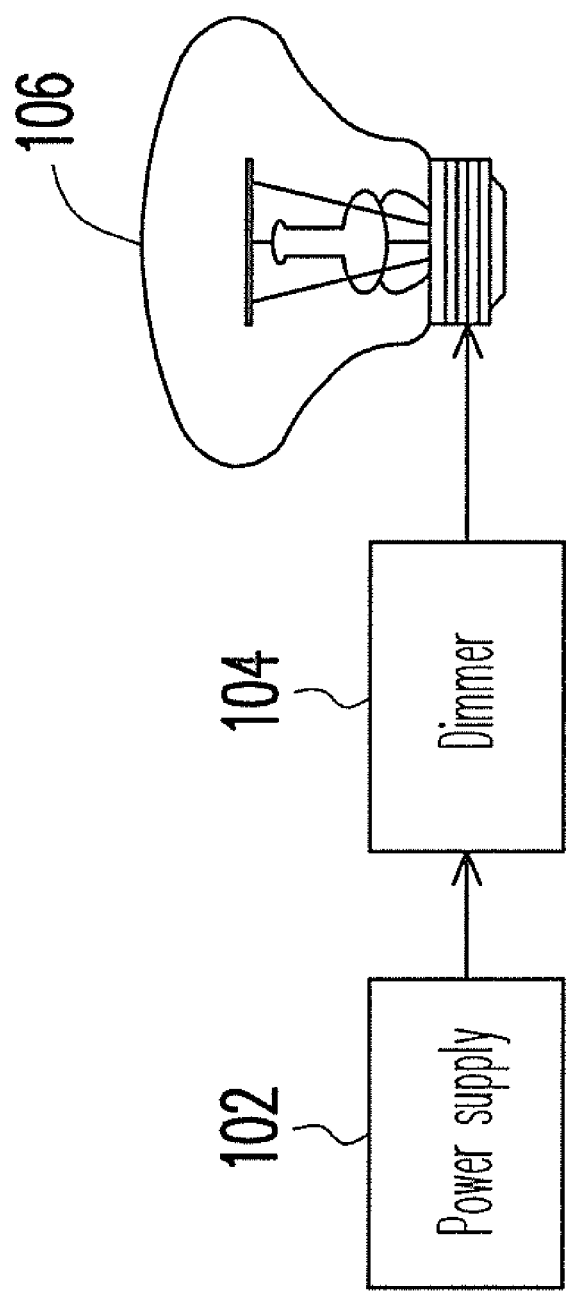
FIG. 1 is a diagram illustrating a conventional lighting apparatus.
Figure 2:
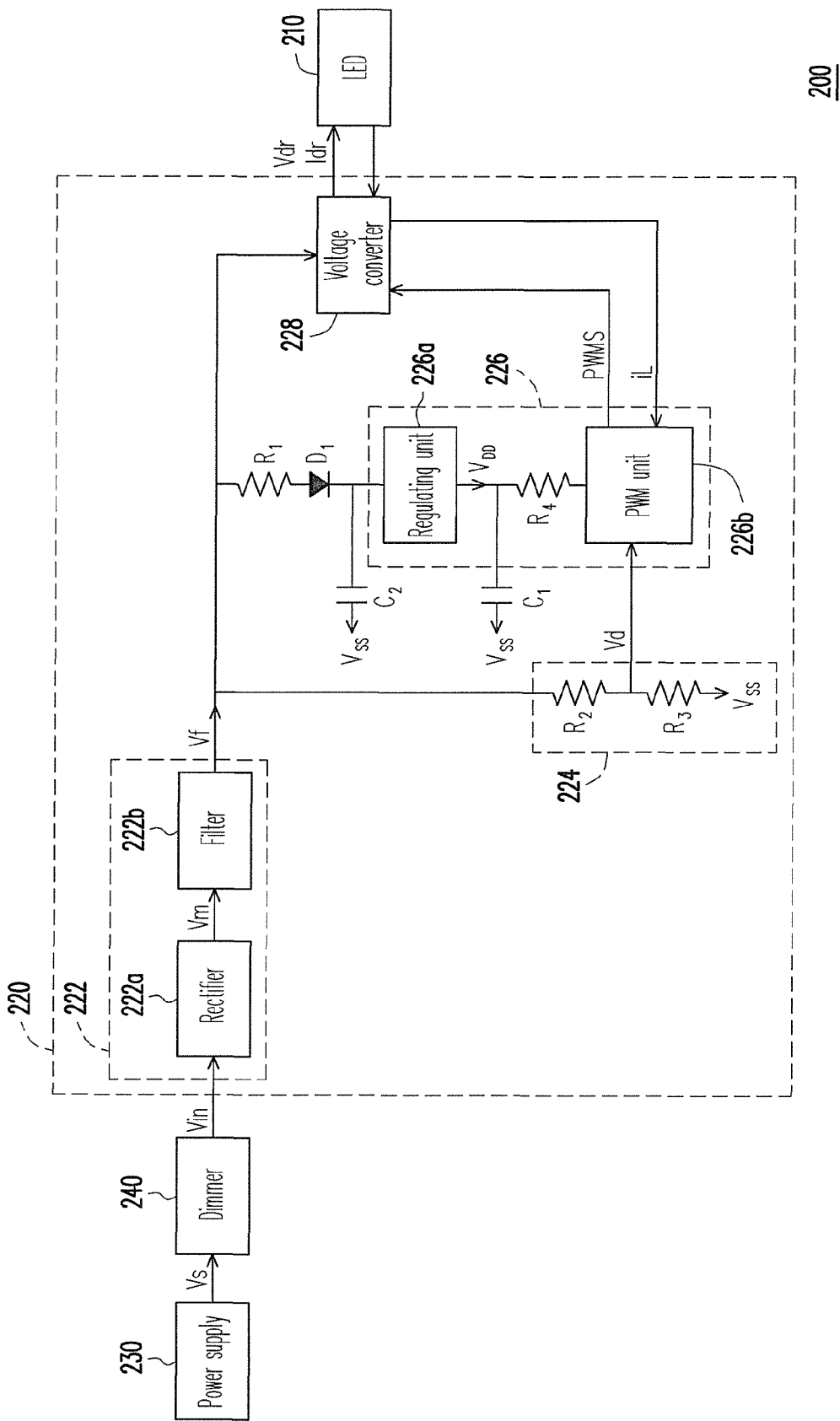
FIG. 2 is a diagram illustrating a lighting apparatus according to an embodiment of the present invention.

FIG. 2 is a diagram illustrating a lighting apparatus according to an embodiment of the present invention. Referring to FIG. 2, the lighting apparatus 200 includes a light emitting diode (LED) 210 and a driving circuit 220. The driving circuit 220 includes a rectifier unit 222, a voltage-dividing circuit 224, a control unit 226, a voltage converter 228, a resistor $R_1$, a capacitor $C_2$ and a diode $D_1$. In the present embodiment, the lighting apparatus 200 can further include a power 230 and a dimmer 240, wherein the dimmer 240 receives an input voltage Vs from the power supply 230, and outputs an alternating current (AC) power Vin according to a conducting condition. In the present embodiment, the dimmer 240 can be implemented by a tri-electrode AC switch (TRIAC), though the present invention is not limited thereto. Moreover, illuminance values of a light source that is adjusted by the TRIAC dimmer are sequentially divided into nine grades of a maximum value, a first to a seventh values and a minimum value, wherein each grade corresponds to a different delay angle α. The greater the delay angle α is, the smaller a conducting angle is, and the longer the dimmer 240 being turned off. Besides, the power 230 can be a local AC power or a power provided by a power supply, which is not limited by the present invention.

In addition, the rectifier unit 222 further includes a rectifier 222a and a filter 222b, wherein the filter 222b is coupled to an output terminal of the rectifier 222a. The rectifier 222a rectifies the AC power Vin to generate a rectified voltage Vm, and transmits it to the filter 222b. The filter 222b outputs a first operating voltage Vf to the voltage-dividing circuit 224, the control unit 226 and the voltage converter 228. Besides, the control unit 226 of the present embodiment further includes a regulating unit 226a and a pulse width modulation (PWM) unit 226b. The regulating unit 226a receives the first operating voltage Vf to output a stable second operating voltage $V_{DD}$ to the PWM unit 226b. On the other hand, the PWM unit 226b generates a PWM signal PWMS to the voltage converter 228 according to a voltage-dividing signal Vd of the voltage-dividing circuit 224 and a feedback signal iL provided by the voltage converter 228. Thereafter, the voltage converter 228 drives the LED 210 and adjusts a driving voltage Vdr and a driving current Idr of the LED 210 according to the PWM signal PWMS.

As shown in FIG. 2, the voltage-dividing circuit 224 includes resistors $R_2$ and $R_3$. The voltage-dividing circuit 224 is coupled to a ground terminal Vss through the resistor $R_3$, and divides the first operating voltage Vf to generate the voltage-dividing signal Vd, wherein the voltage-dividing signal Vd is output to the PWM unit 226b from a common node between the resistors $R_2$ and $R_3$. Moreover, applying of the voltage-dividing circuit 224 can improve a capacitive characteristic of a conventional LED light apparatus, so as to improve a whole power factor (PF) of the light apparatus 200 to about 0.962.

It should be noticed that the capacitor $C_2$ of FIG. 2 is used for storing the driving voltage required by the control unit 226, i.e. the first operating voltage Vf provided by the rectifier unit 222. Therefore, even if the dimmer 240 is adjusted to a position of the minimum (i.e. the TRIAC delay angle α has the maximum value), there still has an enough driving voltage for driving the control unit 226, so as to avoid a flickering phenomenon of the LED 210 generated due to an unstable voltage. On the other hand, the resistor $R_1$ is a current-limiting resistor, and is coupled between an output terminal of the rectifier unit 222 and the diode $D_1$, which can influence a charging time of the capacitor $C_2$. In detail, if the capacitor $C_2$ is required to be quickly charged, the resistor $R_1$ has to be small, wherein the capacitor $C_2$ is coupled between a power input terminal of the regulating unit 226a and the ground terminal Vss. Moreover, another terminal of the diode $D_1$ is coupled to the power input terminal of the regulating unit 226a, which can restrict a flowing direction of the current. Namely, the current flowing through the diode $D_1$ can only flow along a direction from the rectifier unit 222 to the control unit 226. By such means, loss of energy stored in the capacitor $C_2$ through the original charging circuit can be avoided, so as to avoid the original charging path of the capacitor $C_2$ being changed to a discharging path. Similarly, the lighting apparatus 200 of the present embodiment further includes a capacitor $C_1$. The capacitor $C_1$ is coupled between the output terminal of the regulating unit 226a and the ground terminal Vss, which is used for stabilizing the second operating voltage $V_{DD}$ of the PWM unit 226b.

Figure 3A:
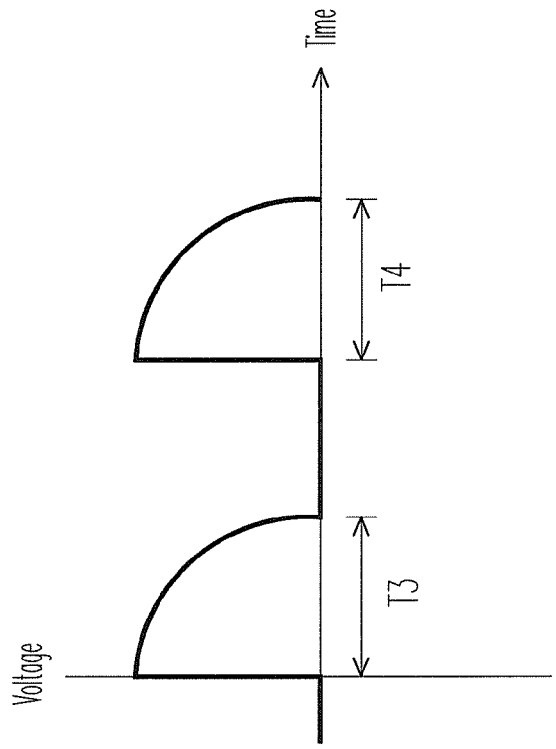
FIG. 3A is a waveform diagram of an AC power Vin.
Figure 3B:
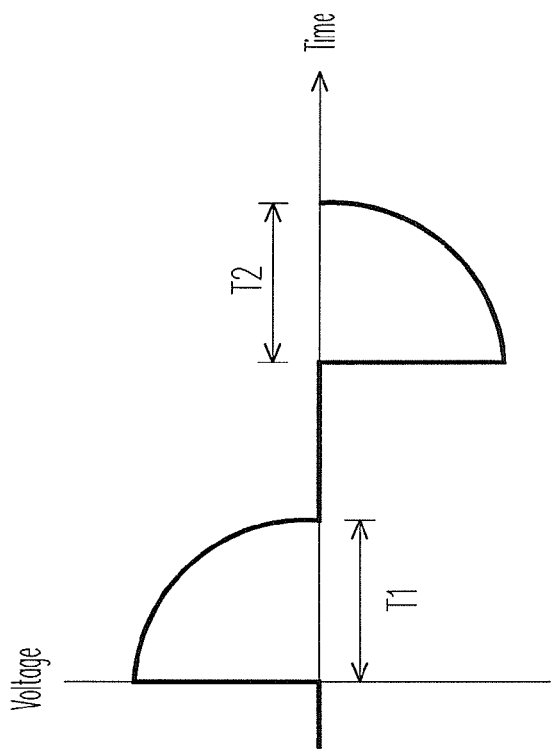
FIG. 3B is a waveform diagram of a rectified voltage Vm.
Figure 3C:
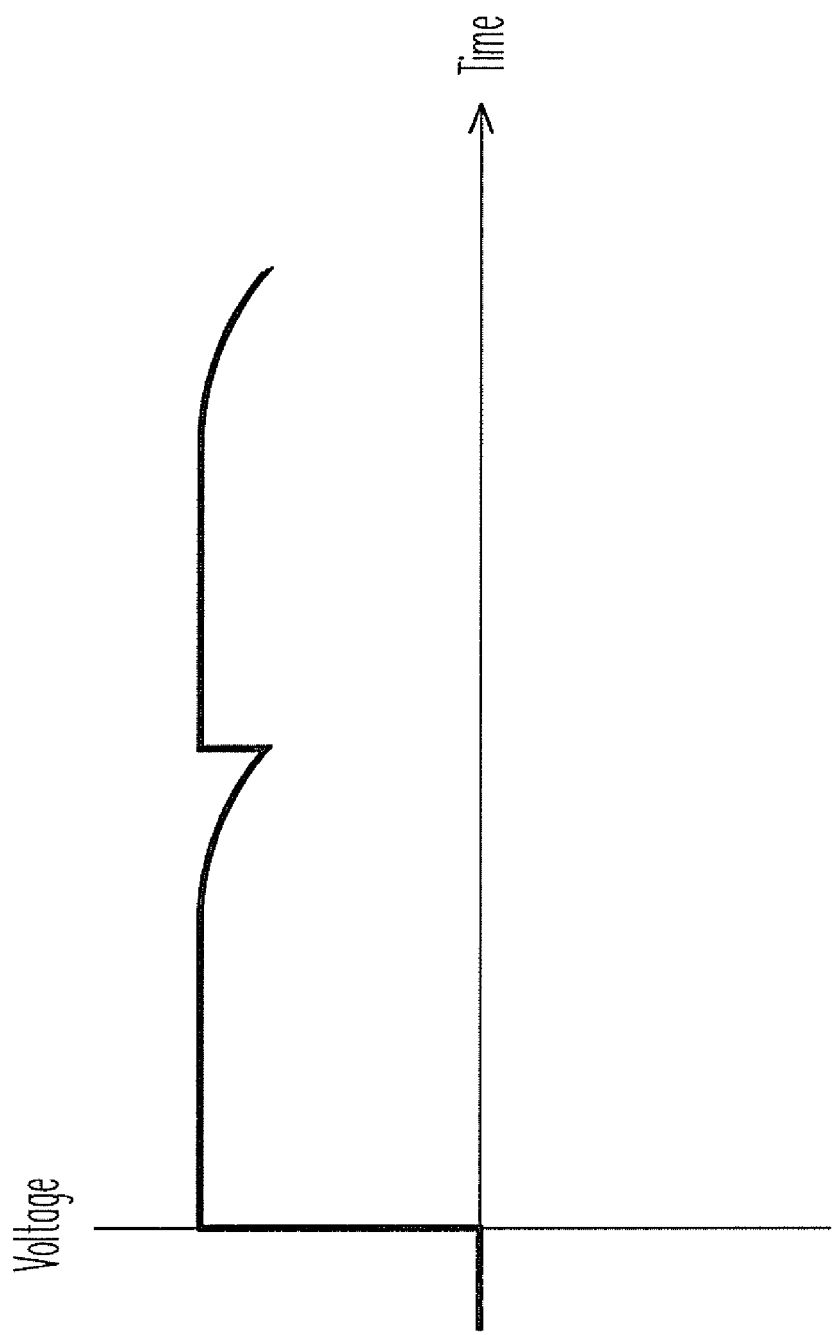
FIG. 3C is a waveform diagram of a first operating voltage Vf.

In order to describe operations of the lighting apparatus 200 of the present embodiment in detail, waveform diagrams of related signals or voltages generated during the operation of the lighting apparatus 200 are illustrated in FIG. 3A to FIG. 3C. FIG. 3A is a waveform diagram of the AC power Vin. Referring to FIG. 2 and FIG. 3A, the dimmer 240 adjusts a duty cycle and a waveform of the AC power Vin by adjusting a conducting condition of the TRAIC. In other words, the dimmer 240 can adjust half duty cycles T1 and T2 of the AC power Vin. Thereafter, the rectifier 222a rectifies the AC power Vin to provide the rectified voltage Vm, wherein a waveform of the rectified voltage Vm is as that shown in FIG. 3B.

Referring to FIG. 2 to FIG. 3B, when the duty cycles and the waveform of the AC power Vin are changed, the duty cycles and the waveform of the rectified voltage Vm are changed accordingly. For example, a duty cycle T3 is varied along with the duty cycle T1, and a duty cycle T4 is varied along with the duty cycle T2. Accordingly, the driving voltage Vdr and the driving current Idr provided to the LED 210 by the rectifier unit 222 are also changed, so that the brightness of the LED 210 is adjusted. In the present embodiment, the rectifier 222a can be a bridge rectifier, though the present invention is not limited thereto.

Besides, the filter 222b receives and filters the rectified voltage Vm to output the first operating voltage Vf to the control unit 226, wherein a waveform of the first operating voltage Vf is as that shown in FIG. 3C. Thereafter, the regulating unit 226a receives the first operating voltage Vf and outputs the second operating voltage $V_{DD}$ for operating the PWM unit 226b.

According to the above descriptions, since the second operating voltage $V_{DD}$ provides an operation power for the PWM unit 226b, the PWM unit 226b can adjust the PWM signal PWMS according to the voltage-dividing signal Vd and the feedback signal iL provided by the voltage converter 228. On the other hand, the voltage converter 228 can adjust the driving voltage Vdr and the driving current Idr according to the PWM signal PWMS, so as to adjust the brightness of the LED 210. Moreover, the driving voltage Vdr and the driving current Idr provided by the voltage converter 228 are relatively stable, so that the LED 210 can provide a stable brightness to mitigate the flicking phenomenon.

In the present embodiment, the voltage converter 228 can be a buck circuit, or can be implemented by a buck converter, though the present invention is not limited thereto. Besides, the voltage converter 228 can output the feedback signal iL to the PWM unit 226b, so that the PWM unit 226b can adjust the PWM signal PWMS with reference of the feedback signal iL. The feedback signal iL includes states of the driving voltage Vdr and the driving current Idr output by the voltage converter 228.

Figure 4A:
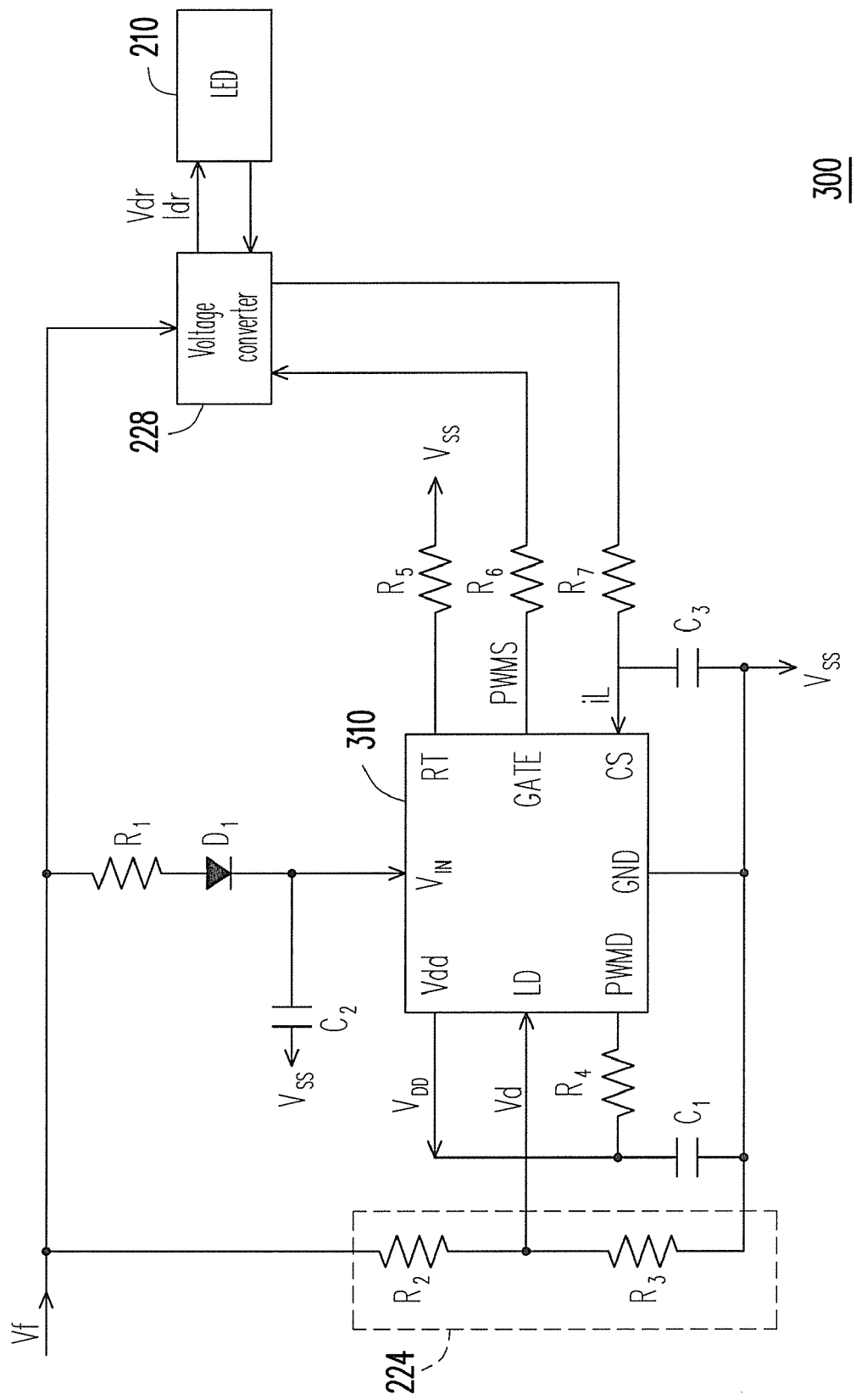
FIG. 4A is a partial circuit diagram of a lighting apparatus according to another embodiment of the present invention.

On the other hand, the control unit 226 of the present embodiment can be implemented by an application-specific integrated circuit (ASIC), though the present invention is not limited thereto. FIG. 4A is a partial circuit diagram of a lighting apparatus 300 according to another embodiment of the present invention. Referring to FIG. 2 and FIG. 4A, the embodiments of FIG. 2 and FIG. 4A are similar, and a difference there between is that a control unit 310 of FIG. 4A is the ASIC. In detail, the control unit 310 is an integration of the regulating unit 226a and the PWM unit 226b of FIG. 2. On the other hand, the lighting apparatus 300 further includes bypass components such as a capacitor $C_3$, resistors $R_5$-$R_7$, which can further stabilize the voltage of the circuit.

Figure 4B:
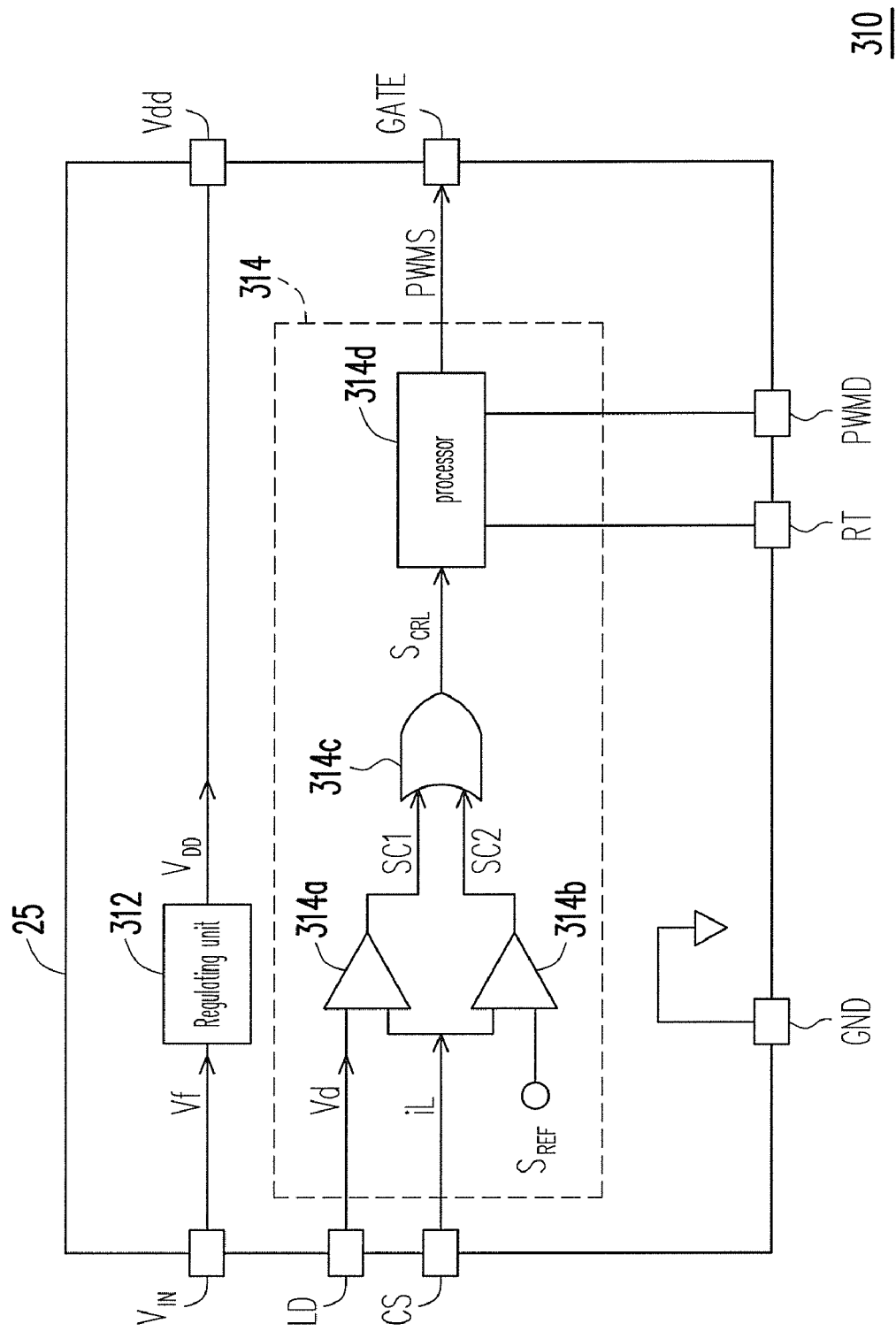
FIG. 4B is a detailed circuit diagram of a control unit of FIG. 4A.

FIG. 4B is a detailed circuit diagram of the control unit 310 of FIG. 4A. Referring to FIG. 4A and FIG. 4B, the control unit 310 is the ASIC, which includes a regulating unit 312 and a PWM unit 314. Moreover, the control unit 310 further includes a plurality of input/output (I/O) ports, which are respectively a power input port $V_{IN}$, a linear dimming port LD, a voltage output port Vdd, a reference signal input port PWMD, a feedback signal input port CS, a ground port GND, a frequency setting port RT and a signal output port GATE, wherein the frequency setting port RT is used for setting an oscillation frequency of the ASIC. The regulating unit 312 is coupled between the power input port $V_{IN}$ and the voltage output port Vdd, and receives the first operating voltage Vf from the rectifier unit 222 (shown in FIG. 2) through the power input port $V_{IN}$, and outputs the second operating voltage $V_{DD}$ through the voltage output port Vdd to serves as the operating voltage of the PWM unit 314.

As shown in FIG. 4B, the PWM unit 314 includes a first comparator 314a, a second comparator 314b, a logic OR gate 314c and a processor 314d. The first comparator 314a receives the voltage-dividing signal Vd from the linear dimming port LD and receives the feedback signal iL from the feedback signal input port CS, and outputs a first comparison signal SC1. The second comparator 314b receives the feedback signal iL from the feedback signal input port CS and receives a reference signal $S_{REF}$, and outputs a second comparison signal SC2.

Then, the logic OR gate 314c outputs a control signal $S_{CRL}$ according to the first comparison signal SC1 and the second comparison signal SC2. The processor 314d is electrically connected to the logic OR gate 314c. In the present embodiment, the processor 314d outputs the PWM signal PWMS through the signal output port GATE according to the control signal $S_{CRL}$. Moreover, as shown in FIG. 4A, the voltage output port Vdd is electrically connected to the reference signal input port PWMD through a resistor $R_4$, and is electrically connected to the capacitor $C_1$. In addition, functions of the resistor $R_1$, the capacitors $C_1$-$C_2$ and the diode $D_1$ are similar as that described in the aforementioned embodiment, and therefore detailed descriptions thereof are not repeated.

Figure 5:
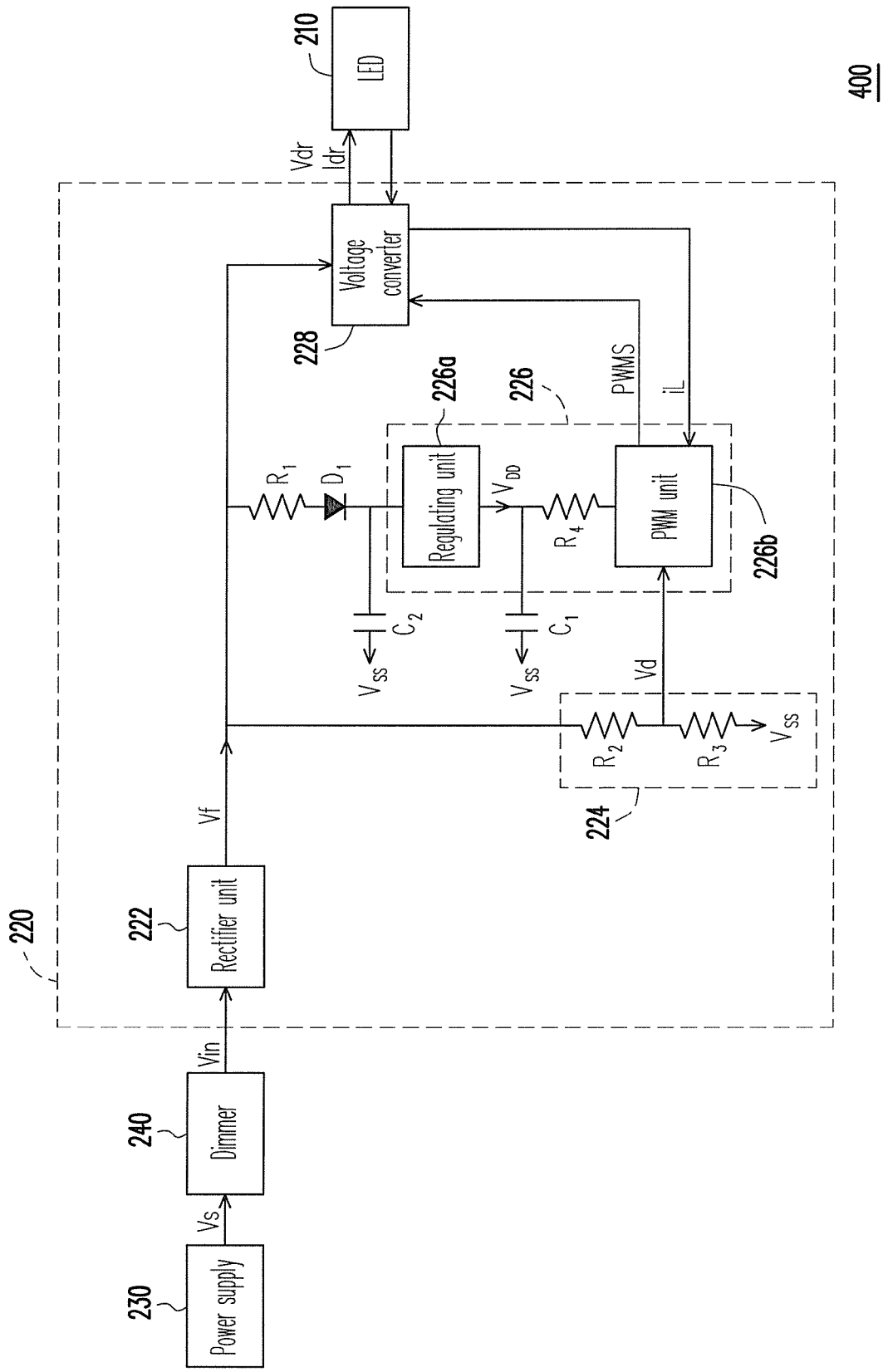
FIG. 5 is a schematic diagram of a lighting apparatus according to another embodiment of the present invention.

FIG. 5 is a schematic diagram of a lighting apparatus 400 according to another embodiment of the present invention. The lighting apparatus 400 is similar to the lighting apparatus 200, while a main difference there between is that the lighting apparatus 400 does not include the filter 222b. Namely, the rectifier unit 222 of the light apparatus 400 is equivalent to the rectifier 222a of the lighting apparatus 200. Therefore, the first operating voltage Vf of the present embodiment is substantially equivalent to the rectified voltage Vm of FIG. 2.

Referring to FIGS. 3A-3B and FIG. 5, according to the above descriptions, a user can adjust the brightness of the LED 210 through the dimmer 240 and the lighting apparatus 220. In detail, the user can adjust the AC power Vin through the dimmer 240, so that the AC power Vin may have the duty cycles T1 and T2. The rectifier 222a rectifies the AC power Vin and outputs the first operating voltage Vf having the duty cycles T3 and T4, wherein the duty cycle T3 is varied along with the duty cycle T1, and the duty cycle T4 is varied along with the duty cycle T2. Thereafter, the control unit 226 can provide the PWM signal PWMS to the voltage converter 228 according to the voltage-dividing signal Vd and the feedback signal iL.

Finally, the voltage converter 228 provides the stable driving voltage Vdr and the driving current Idr, so that the LED 210 can provide the stable brightness to mitigate the flickering phenomenon. By such means, when the AC power Vin received by the rectifier 222a is changed, the driving voltage Vdr and the driving current Idr provided by the voltage converter 228 are accordingly varied. Therefore, the brightness of the LED 210 is accordingly changed, so as to implement a function of adjusting the brightness of the LED 210. It should be noticed that the voltage converter 228 of the present embodiment is directly coupled to the rectifier unit 222 (which is equivalent to the rectifier 222a of FIG. 2). Namely, the first operating voltage Vf of the present embodiment is not filtered by the filter 222b (shown in FIG. 2). Therefore, the driving current Idr of the LED 210 and the first operating voltage Vf output from the rectifier unit 222 has a same phase, wherein waveforms of the first operating voltage Vf and the driving current Idr are as that shown in FIG. 6.

Figure 6:
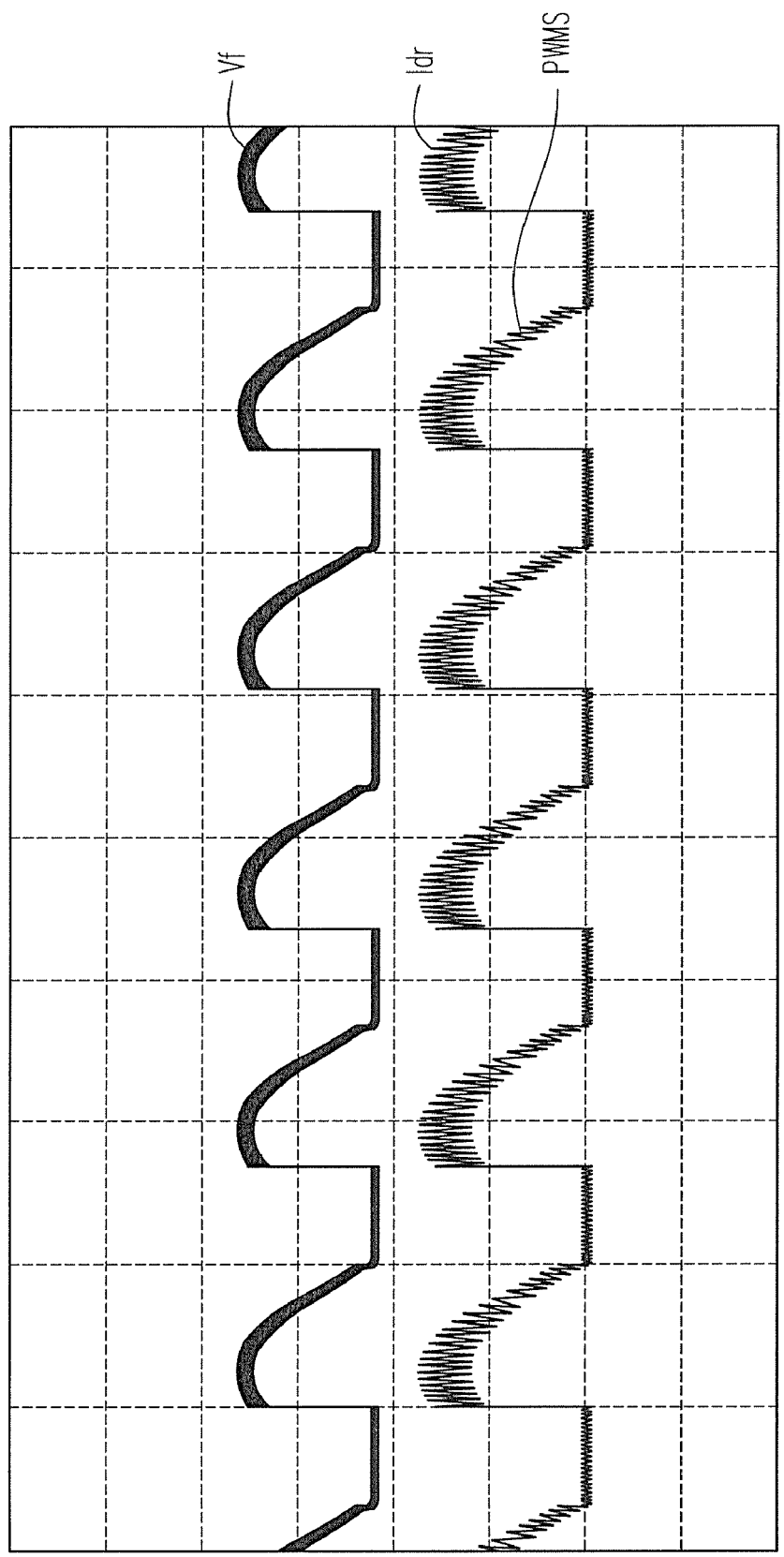
FIG. 6 is a waveform diagram of a first operating voltage and a driving current.

FIG. 6 is a waveform diagram of the first operating voltage Vf and the driving current Idr when the TRIAC dimmer is adjusted to a third position (i.e. the delay angle $\alpha$=64 degrees), wherein the PWM signal PWMS is a sub-carrier on the driving current Idr. The voltage converter 228 controls to turn on/off the LED 210 according to the PWM signal PWMS. As shown in FIG. 6, since the first operating voltage Vf and the driving current Idr has the same phase, the lighting apparatus 400 of the present embodiment may reach a high power factor of 0.962. On the other hand, a dimmable range of the light apparatus 400 can be greatly increased according to such same phase and the hardware linear dimming function.

Figure 7A:
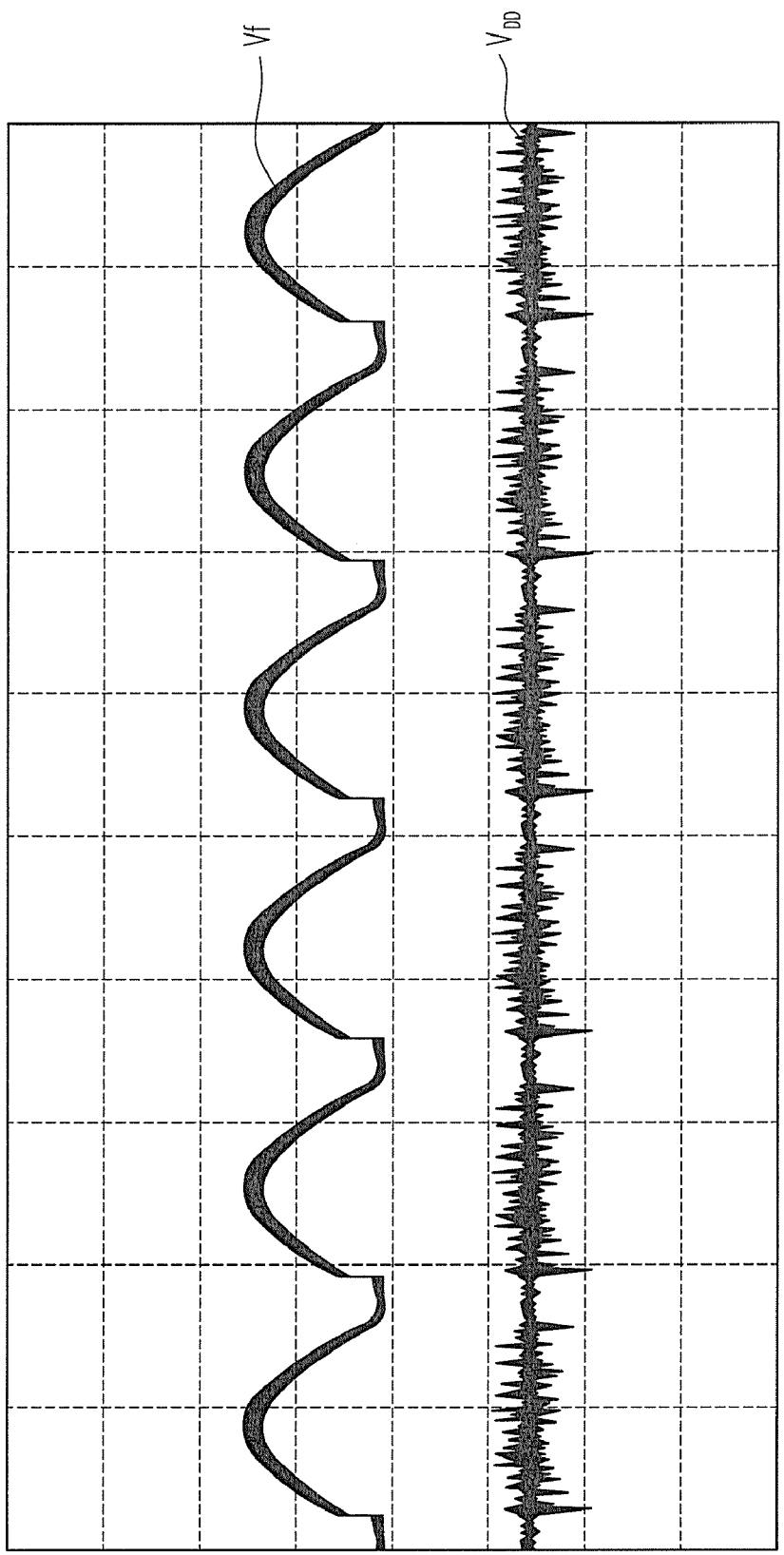
FIGS. 7A-7C are waveform diagrams of a first operating voltage and a second operating voltage.
Figure 7B:
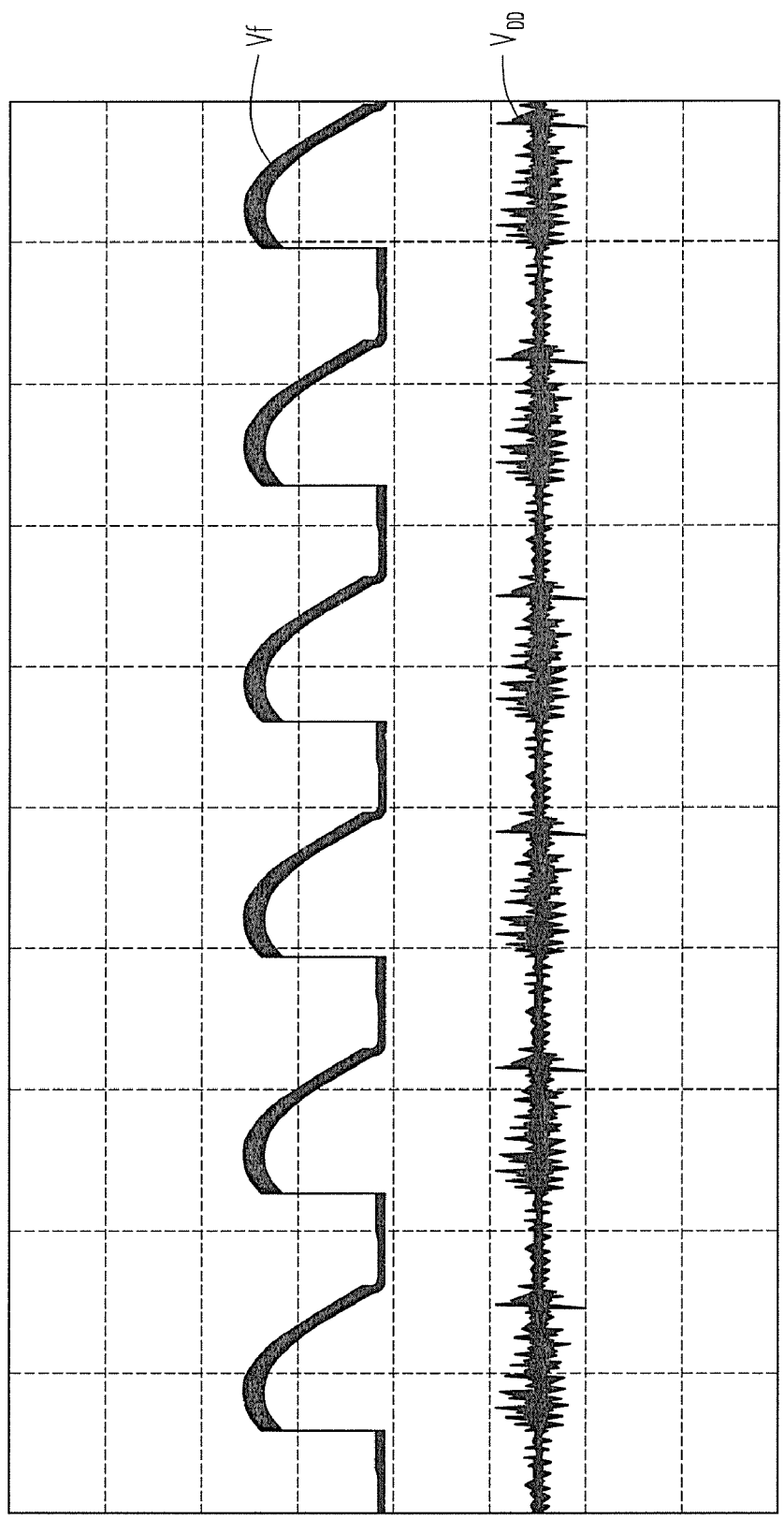
Figure 7C:
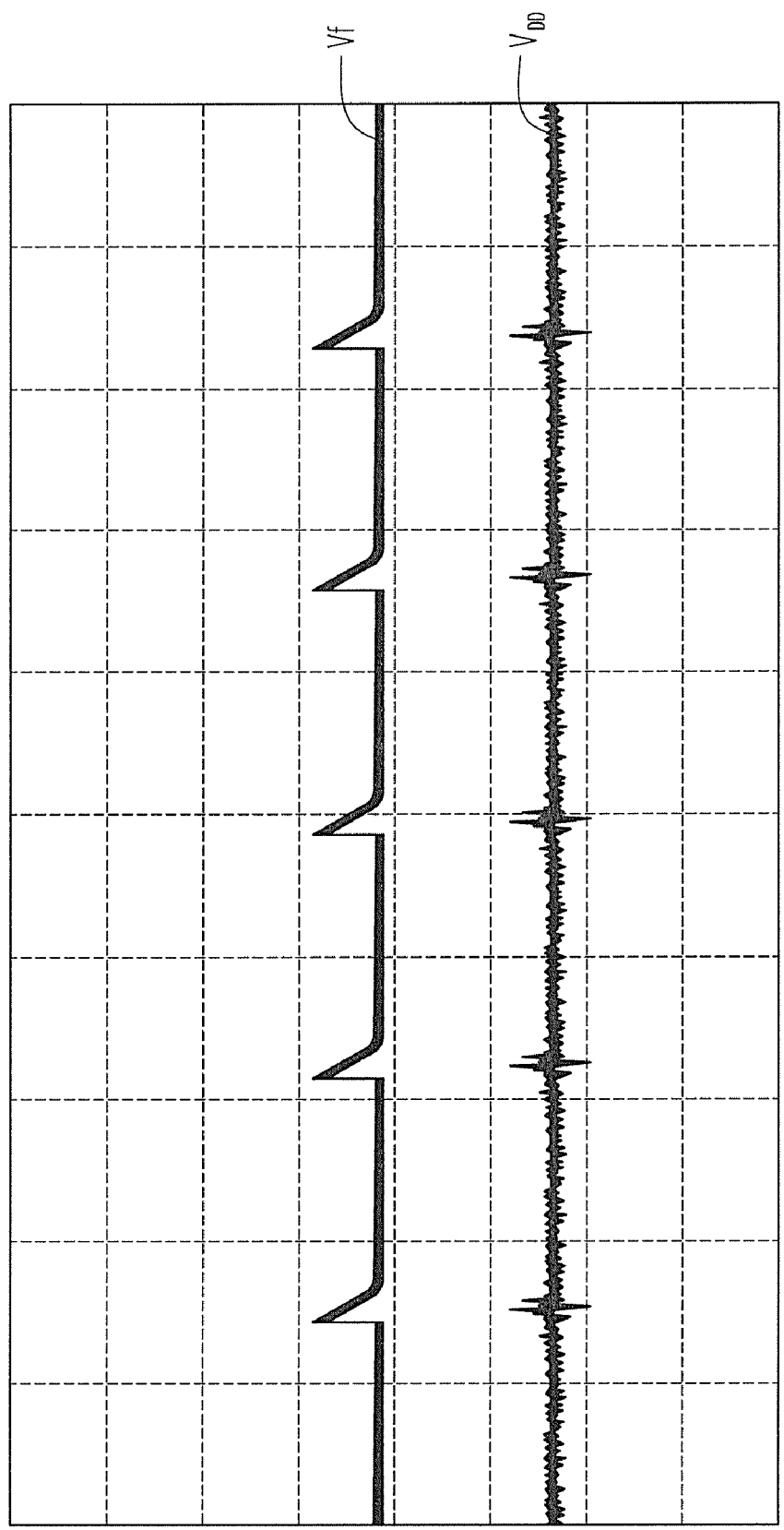

FIGS. 7A-7C are waveform diagrams of the first operating voltage Vf and the second operating voltage $V_{DD}$ of the lighting apparatus 400 under different delay angles $\alpha$. In detail, FIG. 7A, FIG. 7B and FIG. 7C are respectively waveform diagrams of the first operating voltage Vf and the second operating voltage $V_{DD}$ in case that the delay angle $\alpha$=26 degrees (corresponding to the maximum position of the dimmer), $\alpha$=64 degrees (corresponding to the third position of the dimmer) and $\alpha$=155 degrees (corresponding to the minimum position of the dimmer). As shown in FIG. 7A and FIG. 7B, when the delay angle $\alpha$=26 degrees and $\alpha$=64 degrees, the second operating voltage $V_{DD}$ is maintained to a stable voltage of 7.5V, and when he delay angle $\alpha$=155 degrees, the second operating voltage $V_{DD}$ is also maintained to a stable voltage of 7.4V. Therefore, regardless of the conducting condition of the dimmer 250, the control unit 226 can be driven due to that the capacitor $C_2$ (shown in FIG. 4) can provide an adequate voltage, so that the stable driving voltage Vdr and the driving current Idr can be provided to the LED 210. Moreover, the function of the capacitor $C_2$ is as that described in the aforementioned embodiment, and therefore detailed description thereof is not repeated.

In summary, the lighting apparatus of the present invention includes the driving circuit of the LED and the LED, so that the lighting apparatus having the LED can be directly installed on a conventional lamp base, and a light brightness thereof can be adjusted by a conventional dimmer. The lighting apparatus can rectify the AC power provided by the dimmer, and can output the PWM signal according to the first operating voltage and the feedback signal to adjust the voltage converter, so that the voltage converter can provide the stable driving voltage and the driving current to the LED. By such means, not only the brightness of the LED can be adjusted, but also the flickering phenomenon of the LED generated due to waveform variation of the AC power can be avoided. On the other hand, the first operating voltage and the driving current of the lighting apparatus has the same phase, so that a high power factor of the lighting apparatus is achieved, and a dimmable range thereof is increased.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A driving circuit of a light emitting diode (LED), adapted to receive an AC power to drive the LED, the driving circuit comprising:
a rectifier unit, rectifying the AC power to generate a first operating voltage;
a voltage-dividing circuit, coupled to the rectifier unit for receiving the first operating voltage to generate a voltage-dividing signal corresponding to the first operating voltage;
a control unit, comprising a regulating unit and a pulse width modulation (PWM) unit, wherein an output terminal of the regulating unit is coupled to the PWM unit, and the PWM unit outputs a PWM signal;
a voltage converter, coupled between the control unit and the LED for driving the LED, and adjusting a driving voltage and a driving current of the LED according to the PWM signal;
a resistor, coupled between an output terminal of the rectifier unit and a diode, and another terminal of the diode being coupled to a power input terminal of the regulating unit; and
a first capacitor, coupled between the power input terminal of the regulating unit and a ground terminal,
wherein the PWM unit adjusts the PWM signal according to the voltage-dividing signal and a feedback signal output by the voltage converter.

2. The driving circuit as claimed in claim 1, further comprising a second capacitor coupled between an output terminal of the regulating unit and the ground terminal.

3. The driving circuit as claimed in claim 1, wherein the voltage converter is coupled to the output terminal of the rectifier unit.

4. The driving circuit as claimed in claim 1, wherein the rectifier unit comprises a rectifier for rectifying the AC power to generate a rectified voltage.

5. The driving circuit as claimed in claim 4, wherein the rectifier unit further comprises a filter coupled to an output terminal of the rectifier for receiving the rectified voltage to output the first operating voltage to the voltage converter.

6. The driving circuit as claimed in claim 4, wherein the rectified voltage is substantially equivalent to the first operating voltage.

7. The driving circuit as claimed in claim 1, wherein the regulating unit receives the first operating voltage to output a second operating voltage to the PWM unit.

8. The driving circuit as claimed in claim 1, wherein the control unit is an application-specific integrated circuit (ASIC).

9. The driving circuit as claimed in claim 1, wherein the voltage converter is a buck circuit.

10. The driving circuit as claimed in claim 1, wherein the AC power is an AC power adjusted by a dimmer.

11. A lighting apparatus, adapted to receive an AC power for lighting, the lighting apparatus comprising:
an LED; and
a driving circuit, coupled to the LED, and the driving circuit comprising:
a rectifier unit, rectifying the AC power to generate a first operating voltage;

a voltage-dividing circuit, coupled to the rectifier unit for receiving the first operating voltage to generate a voltage-dividing signal corresponding to the first operating voltage;

a control unit, comprising a regulating unit and a PWM unit, wherein an output terminal of the regulating unit is coupled to the PWM unit, and the PWM unit outputs a PWM signal;

a voltage converter, coupled between the control unit and the LED for driving the LED, and adjusting a driving voltage and a driving current of the LED according to the PWM signal;

a resistor, coupled between an output terminal of the rectifier unit and a diode, and another terminal of the diode being coupled to a power input terminal of the regulating unit; and a first capacitor, coupled between the power input terminal of the regulating unit and a ground terminal, wherein the PWM unit adjusts the PWM signal according to the voltage-dividing signal and a feedback signal output by the voltage converter.

12. The lighting apparatus as claimed in claim 11, further comprising a second capacitor coupled between an output terminal of the regulating unit and the ground terminal.

13. The lighting apparatus as claimed in claim 11, wherein the voltage converter is coupled to the output terminal of the rectifier unit.

14. The lighting apparatus as claimed in claim 11, wherein the rectifier unit comprises a rectifier for rectifying the AC power to generate a rectified voltage.

15. The lighting apparatus as claimed in claim 14, wherein the rectifier unit further comprises a filter coupled to an output terminal of the rectifier for receiving the rectified voltage to output the first operating voltage to the voltage converter.

16. The lighting apparatus as claimed in claim 14, wherein the rectified voltage is substantially equivalent to the first operating voltage.

17. The lighting apparatus as claimed in claim 14, wherein the regulating unit receives the first operating voltage to output a second operating voltage to the PWM unit.

18. The lighting apparatus as claimed in claim 14, wherein the control unit is an ASIC.

19. The lighting apparatus as claimed in claim 14, wherein the voltage converter is a buck circuit.

20. The lighting apparatus as claimed in claim 14, wherein the AC power is an AC power adjusted by a dimmer.

* * * * *